United States Patent [19]

Stone

[11] Patent Number: 4,713,974
[45] Date of Patent: Dec. 22, 1987

[54] AUTOSAMPLER

[75] Inventor: Stanley A. Stone, State College, Pa.

[73] Assignee: Varian Associates, Inc./Scientific Systems, Inc., Palo Alto, Calif.

[21] Appl. No.: 853,493

[22] Filed: Apr. 18, 1986

[51] Int. Cl.⁴ ............................................. G01N 30/24
[52] U.S. Cl. ............................. 73/864.23; 73/61.1 C; 73/863.01; 73/864.21; 73/864.84; 73/864.86; 422/64; 422/67; 422/81
[58] Field of Search ............ 73/864.23, 864.87, 864.81, 73/864.82, 864.83, 864.84, 864.21, 864.85, 61.1 C, 864.86, 863.01; 422/64, 67, 70, 81, 82

[56] References Cited

U.S. PATENT DOCUMENTS

| | | |
|---|---|---|
| 3,842,680 | 10/1974 | Vollick et al. . |
| 3,909,203 | 9/1975 | Young et al. . |
| 3,954,012 | 5/1976 | Christen et al. . |
| 3,960,020 | 6/1976 | Gordon et al. . |
| 3,991,627 | 11/1976 | Laird et al. ................... 73/864.23 X |
| 4,094,641 | 6/1978 | Friswell . |
| 4,276,260 | 6/1981 | Drbal et al. ................... 73/864.25 X |
| 4,294,126 | 10/1981 | Tomoff et al. ................... 73/864.21 |
| 4,323,537 | 4/1982 | Mody ................... 422/63 |
| 4,429,584 | 2/1984 | Beyer et al. ................... 73/864.21 |
| 4,478,095 | 10/1984 | Bradley et al. ................... 73/864.21 |

FOREIGN PATENT DOCUMENTS 2069974A 9/1981 United Kingdom .

Primary Examiner—Tom Noland
Attorney, Agent, or Firm—Stanley Z. Cole; Gerald M. Fisher; David Schnapf

[57] ABSTRACT

An improved microprocessor-controlled autosampler for use in liquid chromatography is shown. The autosampler is fully programmable by the operator and capable of performing complex sample preparation routines. A spring-loaded sample needle is employed to ensure that the needle makes contact with the bottom of the sample vial as required, for example, when handling extremely small samples. A hollow vial lifter serves as the receptacle for waste wash solvent eliminating the need for a special waste receptacle mechanism. Other improved features include a plurality of interchangeable, codable sample racks, a four-way valve in the syringe line enabling rapid priming/purging of the hydraulics, and as improved vial stabilizer design.

19 Claims, 10 Drawing Figures

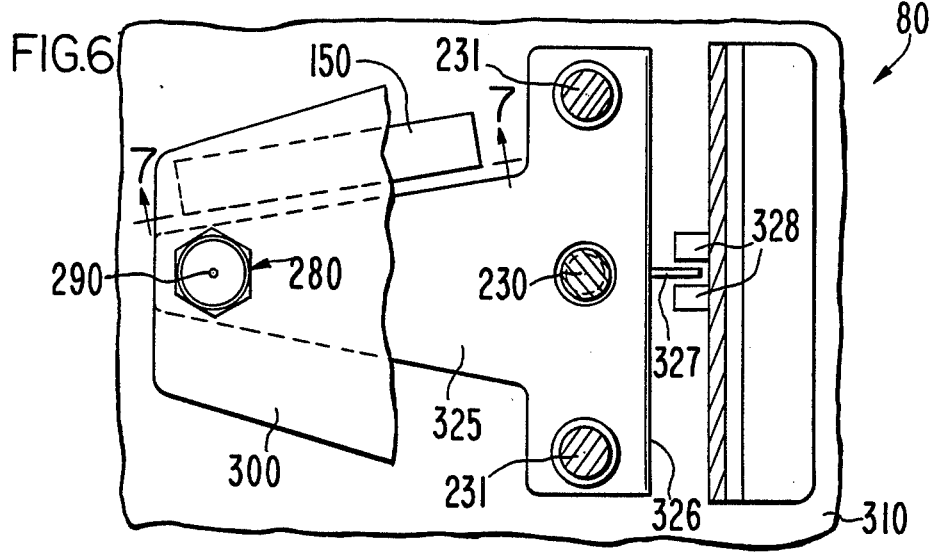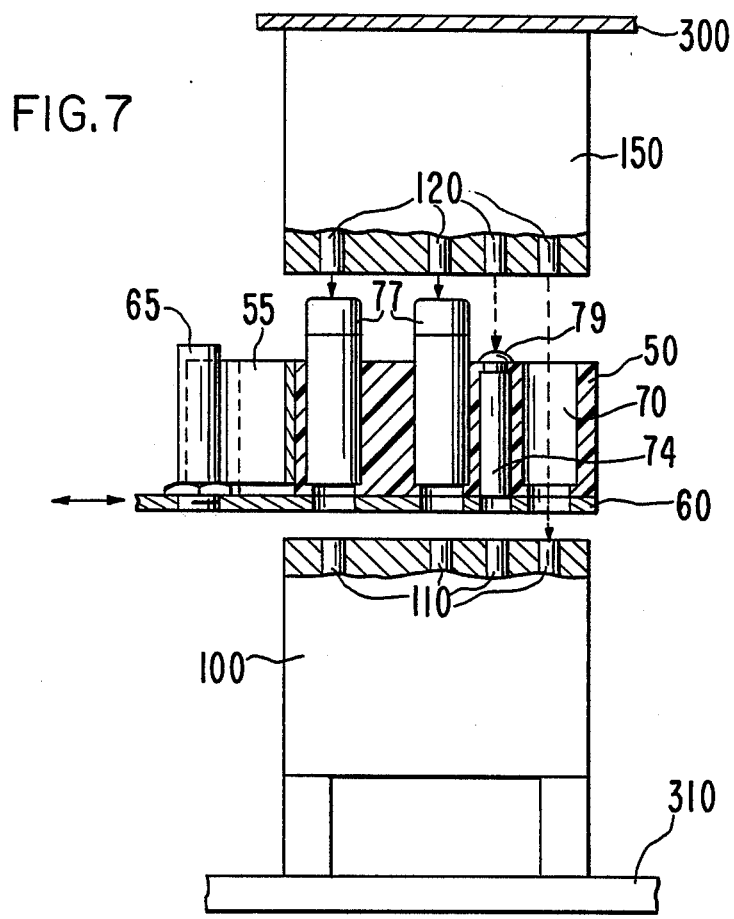

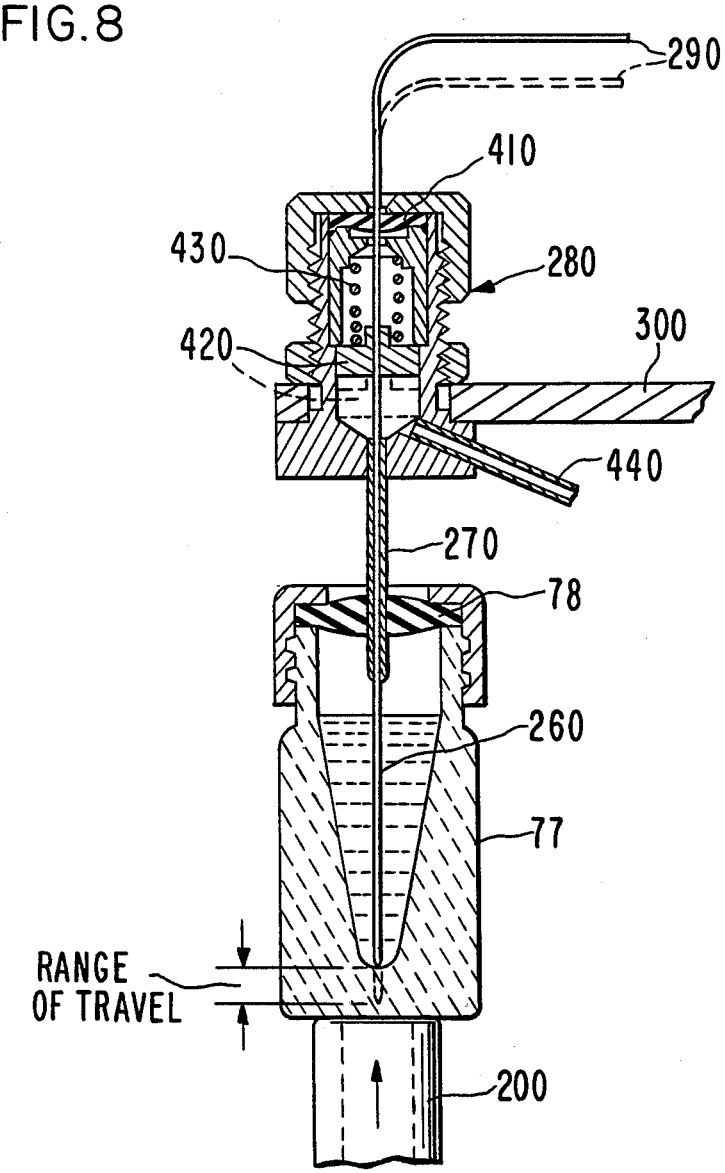

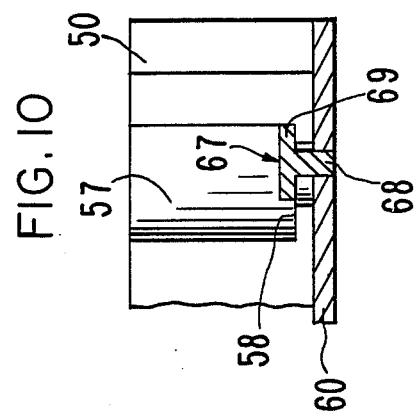
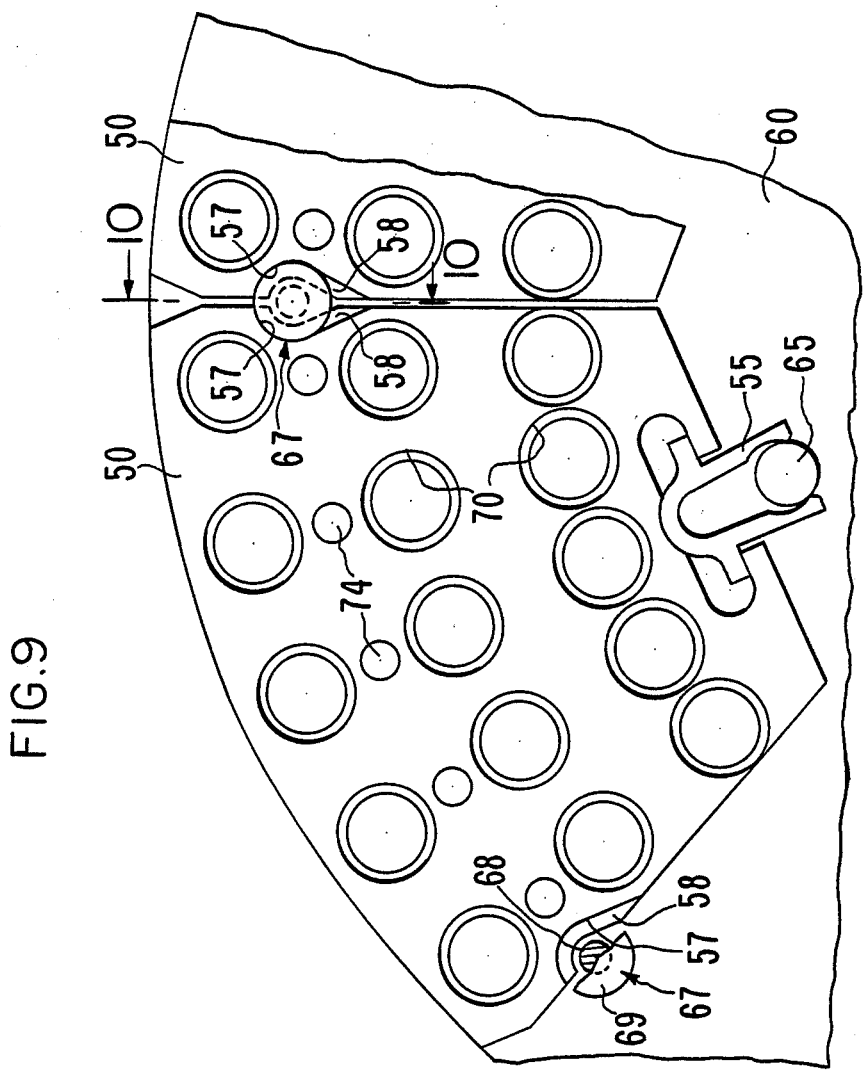

AUTOSAMPLER

BACKGROUND OF THE INVENTION

This invention relates to apparatus and methods for automatically processing a plurality of liquid samples, with particular application to liquid chromatography.

The trend in modern liquid chromatography is towards higher resolution columns and higher sensitivity detectors. Samples with a volume of less than five microliters can now be processed to produce meaningful analytical results. With the capability to process small samples has come the demand for automated methods and apparatus for doing so.

Prior art autosamplers typically employ a circular tray capable of carrying a plurality of sample vials and a needle structure hydraulically connected to the input of a chromatography column. The sample vials are typically covered by septums to preserve the integrity of the samples. The needle is inserted into the vial, either by lifting the vial and impaling it on the needle, or by moving the needle assembly into the vial. When the needle is thus within the sample, the sample is withdrawn. This has been done either by aspirating the sample using a syringe, or by pressurizing the head space of the vial and forcing the liquid into the needle, or by combining pressurization and aspiration. Two needles, often concentrically configured, are sometimes used. The second needle is used either as a source of pressurized gas, or if aspiration is the sole means of sample withdrawal, to vent the head space to atmospheric pressure. The withdrawn sample may then be directed to a sample loop injection valve for injection into the liquid chromatograph. When handling very small samples one may only partially fill the sample loop to avoid any waste.

In order to efficiently utilize extremely small samples, it is necessary for the needle to extend to the very bottom of the vial. In addition, specially designed microvials having conical interiors are designed to handle such samples. Variations in vial designs, and in the manufacturing tolerances in a single vial design are such that it is very difficult to precisely control the location of the needle within the vial. If the needle is spaced apart from the bottom of the vial, valuable sample can be wasted. On the other hand, it is easy to break or bend a fragile sample needle by striking it on the bottom of the vial. One prior art solution to this problem employs vials having spring-loaded sample-containing inserts. When the needle engages the bottom of such a vial the entire insert moves downward minimizing the risk of needle breakage/bending. This approach involves a rather complex vial design with attendent high manufacturing costs.

Normally, it is necessary to wash the needle between sample withdrawals to avoid cross-contamination of samples. This is done by flowing a relatively large volume of wash solvent through the needle. The solvent used for this purpose becomes contaminated and must be disposed of as waste. In prior art autosamplers, waste solvent was disposed of into a special receptacle, or a particular carousel position was assigned to receive the waste. In the former case an additional mechanism was required in the autosampler, while in the latter case, the carousel must be rotated to the designated position resulting in time delays and considerable "busy-work" for the carousel.

Another trend in modern chromatographic analysis has been towards greater sample preparation prior to column injection. The need for precise control over the various sample preparation techniques is compounded when working with extremely small sample volumes. Until now most sample preparation has been done manually which is both less precise and more time-consuming than automated methods.

Accordingly, it is the object of the present invention to provide an autosampler mechanism for use in liquid chromatography which is capable of handling extremely small samples.

Another object of this invention is to provide a mechanism whereby the sample withdrawal needle will engage the bottom of the sample vial without risk of breaking or deforming the needle and without resort to complex vial designs.

Yet another object of this invention is to provide an autosampler with the ability to handle waste solvent from needle washing without resort to additional waste receptacle mechanisms or dedicating a carousel position to waste receipt.

Yet other objects of this invention will be apparent upon reading the following specification and claims.

SUMMARY OF THE INVENTION

The present invention involves an improved microprocessor-controlled autosampler capable of handling extremely small samples and able to perform complex sample preparation routines.

In the autosampler of the present invention, a plurality of samples are held in individual racks which are placed on a carousel tray. A separate "priority" rack for receiving a single sample vial is provided. When one or more of the racks are placed in position and the cover of the autosampler is closed, the apparatus first conducts an inventory of the trays and of which tray positions are occupied with sample vials. This information is then stored in memory. These inventory operations are conducted using an optical sensing system.

The autosampler includes an onboard microprocessor, memory and resident programs stored in read only memory (ROM) for controlling the apparatus. By using a control panel the operator is able to specify a variety of sampling routines for the vials. The user specifies the order of sampling, the volume of sample to be withdrawn and the order of injection of the samples into the liquid chromatograph. Vials can be accessed randomly in any desired order. In addition, the user is able to program sample preparation routines as desired. Examples of possible sample preparation routines include transferring any desired volume of reagents, diluents or standards from selected vials into other vials containing samples of interest. Alternately two vials containing different reactants can be accessed and their contents transferred to a third vial. Liquid/liquid extractions can be specified. In any situation where reactions are occurring precise reaction time can be controlled. Finally, mixing routines are available whenever liquids are combined. The operator's instructions are stored in memory for implementation.

The vial containing the liquid to be utilized, either for sample preparation or injection, is positioned underneath a stationary needle assembly. A vial lifter picks up the vial from below and elevates it. The vial first engages a vial stabilizer, and then is impaled on a needle assembly. The needle assembly comprises two concentric needles. The outer needle is shorter than the inner needle such that when the inner needle is in the sample the open end of the outer needle is in the vial head space providing means for maintaining the head space at atmospheric pressure. As the outer needle approaches the surface of the septum a burst of pressurized gas is flowed through the space between the needles. This burst of gas blows away any fluid or other matter which may be on the septum or on the surface of the inner needle. The needle assembly is of simple design allowing easy replacement and maintenance of needles. For example, the operator may easily change to a wide-bore needle for handling viscous samples.

The vial stabilizer assembly is designed to maintain a constant force on the vial top throughout the entire time it is engaged. In prior art vial stabilizers the vial engaged a fixed spring which exerted an increasing force as the spring was compressed. The increasing spring force created a somewhat greater risk of vial breakage. The overall design of the vial lifter/stabilizer assembly is physically open to allow easy visual inspection and maintenance and to prevent jamming of the mechanism if a vial breaks or otherwise gets caught.

The inner needle is spring-loaded over a limited range of travel so that it will move in an upward direction when it contacts the bottom of the vial. By utilizing the spring-loaded design, the present invention ensures that the needle extends to the vial bottom while, at the same time, it avoids the problem of needle damage. The range of travel of the spring-loaded inner needle is set to encompass the variations in vial designs and in vial manufacturing tolerances.

When the vial is fully elevated, liquid in the sample vial is then withdrawn by aspiration using a motor-driven syringe mechanism controlled by the microprocessor and programmed as described above. The withdrawn fluid is then either directed to the liquid chromatograph column or is used in a sample preparation routine as programmed by the operator. A standard loop injection valve is employed for sample injection. In addition, a four-way valve is located near the syringe to connect to a solvent source and to provide a means for rapid manual purging and priming of the hydraulic system.

After the fluid withdrawn from the vial has been directed to its intended location, a wash cycle is performed to clean the needle. This is done by flowing an operator programmable amount of solvent through the needle. The vial carousel is translated out of the way of the vial lifting mechanism, and the vial lifter is raised to surround the inner needle. The vial lifter is hollow and is connected to a waste drain line. Waste solvent is discharged directly into the hollow vial lifter. After the programmed number of wash cycles are complete the vial lifter is retracted and the unit is ready; to access the next programmed position.

Other aspects of the present invention will be apparent to those skilled in the art upon reading the following detailed description and claims. While the description and drawings are of a preferred embodiment of the invention, other embodiments fall within the scope of the invention.

BRIEF DESCRIPTION OF THE DRAWINGS

FIG. 6 is a cross-sectional plan view partially broken away of the vial lifting assembly along line 6—6 of FIG. 3.

FIG. 7 is a fragmentary side view partially broken away of the vial sensing mechanism of the present invention along line 7—7 of FIG. 6.

FIG. 8 is a fragmentary cross-sectional view of the spring-loaded needle assembly of the present invention.

FIG. 9 is a fragmentary plan view of the carousel plate and a vial rack of the present invention.

FIG. 10 is a fragmentary cross-sectional view of a stabilizer post of the present invention along line 10—10 of FIG. 9.

DETAILED DESCRIPTION OF THE PREFERRED EMBODIMENT

Figure 1:
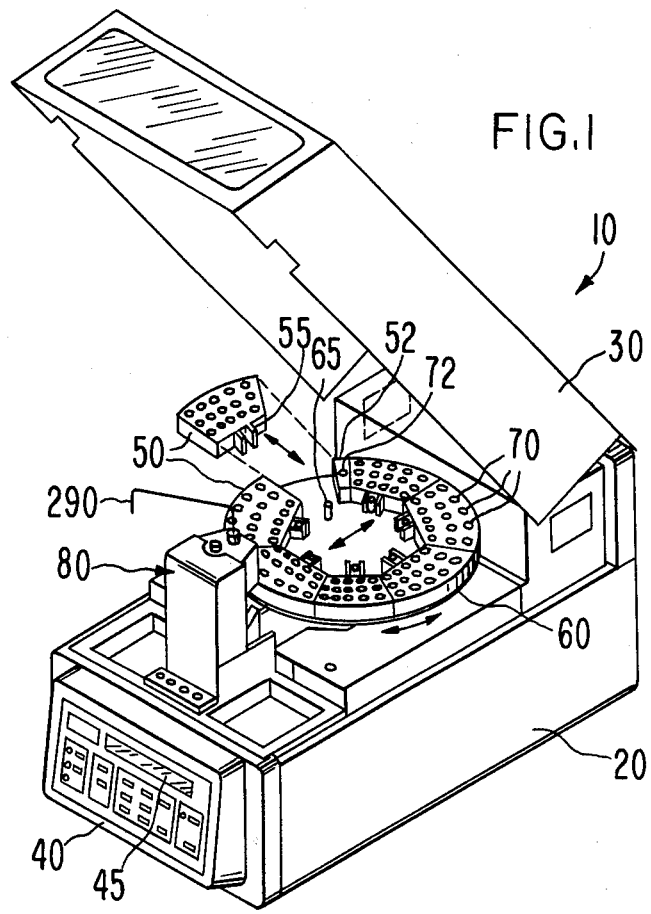
FIG. 1 is a perspective view of the autosampler apparatus of a preferred embodiment of the present invention.

The overall autosampler apparatus of the present invention is depicted in FIG. 1. The autosampler 10 comprises a housing 20 and a cover 30. A control panel 40 on the front of the machine has an alphanumeric display 45, and a plurality of switches enabling the operator to program the apparatus to perform the desired functions. The programming is menu-driven via alphanumeric display 45.

Figure 4:
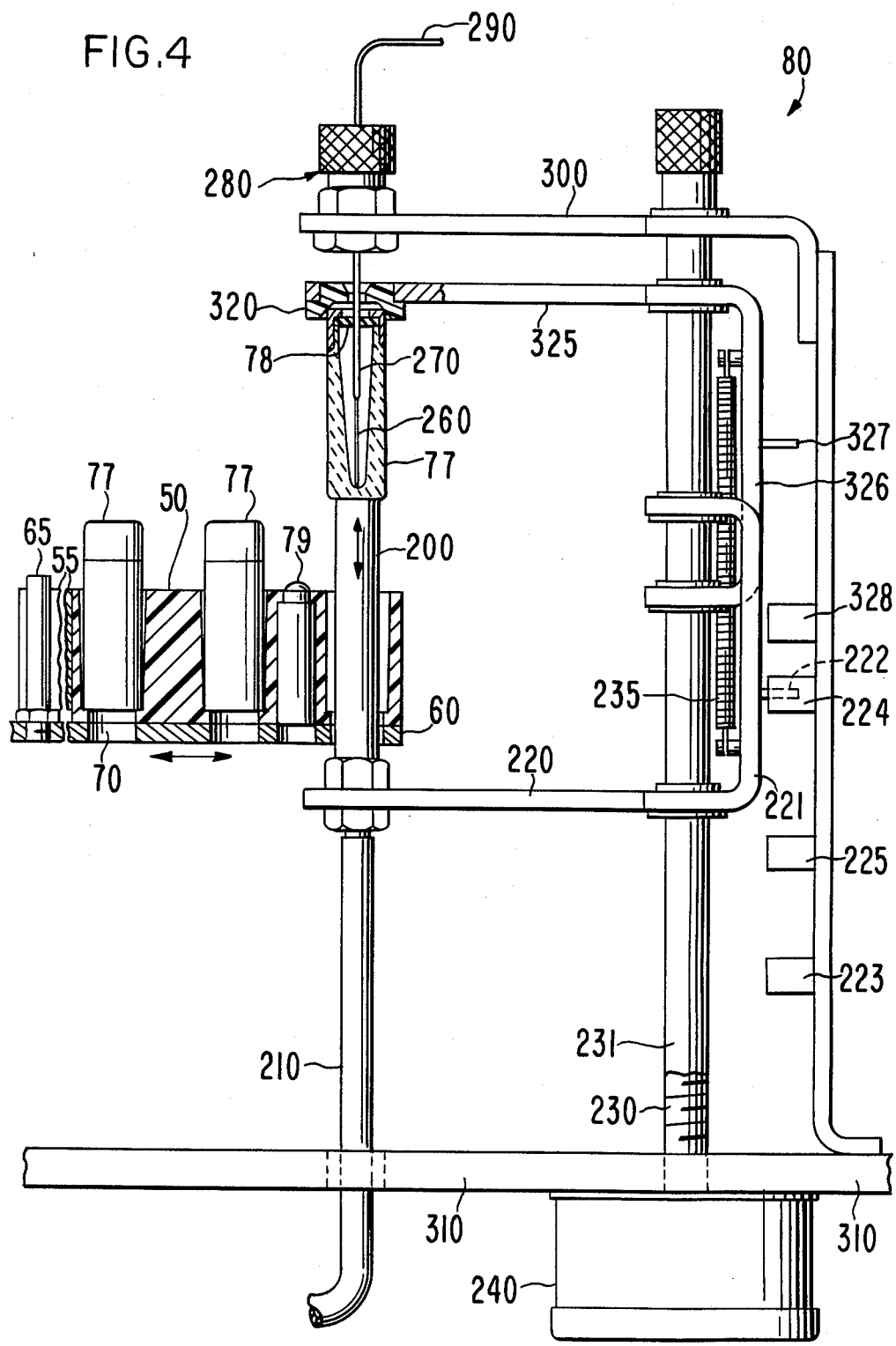
FIG. 4 is a cross-sectional side view of the vial lifting/needle assembly mechanism of the present invention with a vial raised onto the needle assembly.

A plurality of individual racks 50 may be mounted on carousel plate 60 and are held in place by spring clips 55 extending radially inwardly from the racks and which engage posts 65 mounted on the carousel plate 60. Details of the rack structure are described below in reference to FIGS. 9 and 10. The racks contain a plurality of cylindrical recesses 70 for receiving sample vials 77. A priority rack 52, containing a single recess 72 for a priority sample vial is also mounted on the carousel plate 60. All the sample recesses have circular openings at their bottoms of a diameter wide enough to allow the passage of vial lifter 200, but small enough to support the vials 77 as shown in FIG. 4.

Carousel plate 60 can be rotated and can be translated toward or away from the needle/vial lifter assembly 80. The rotational and translational movements are subject to microprocessor control. The microprocessor executes programs stored in ROM and subject to the input routines specified by the operator and stored in memory. Through a combination of rotational and translational movements of carousel plate 60 any vial position can be aligned with a needle/vial lifter assembly 80. In addition, the carousel plate can be translated away from the needle/vial lifter assembly 80, to allow the discharge of waste wash solvent from the needle into the raised vial lifter 200 as described below.

Samples to be analyzed and any other materials used in sample preparation are placed in vials 77 which are inserted into the recesses 70 in sample racks 50. One or more of the racks are then clipped onto the carousel plate 60. Cover 30 is closed and autosampler operation is begun. The operator then specifies the sampling routines and the sample preparation routines by interacting with a menu-driven alphanumeric display 45 on the control panel 40. A vial containing a priority sample can be placed in the priority rack 52 at any time and will be taken for analysis as the next sample without causing any disruption of the remaining sampling program.

Figure 2:
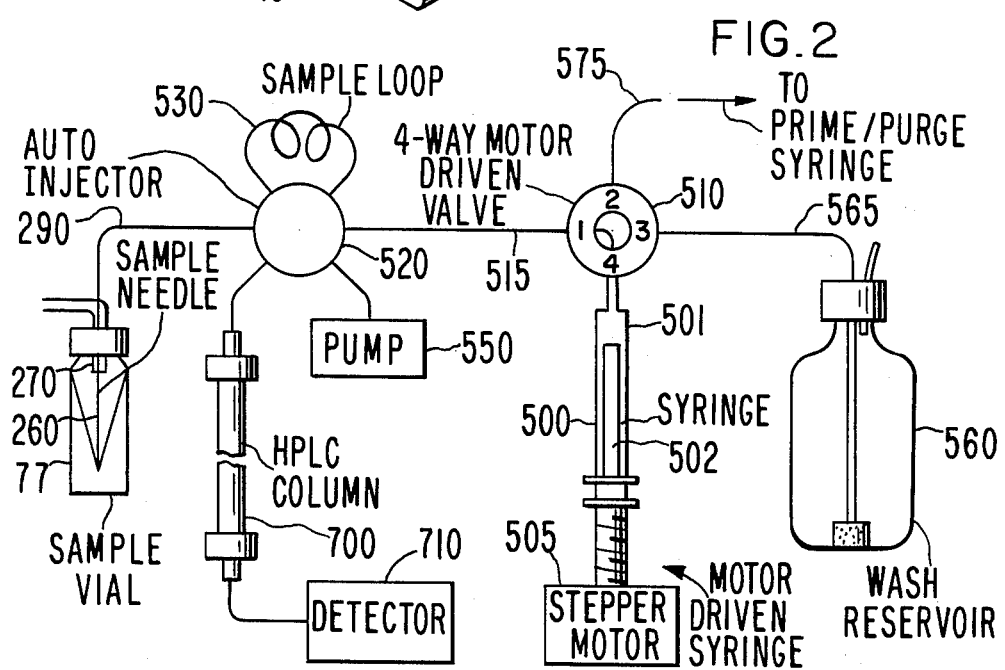
FIG. 2 is a schematic drawing of the hydraulic system of the present invention.

FIG. 2 is a schematic diagram of the hydraulic system of the present invention. To withdraw sample from sample vial 77, four-way valve 510 is set to connect syringe 500 to sample loop injection valve 520, via tubing 515. Syringe 500 has a plunger 502 and a barrel 501. Sample loop injection valve 520 is a standard six-port valve available from a variety of sources such as Scientific Systems, Inc., Valco or Rheodyne.

The sample loop injection valve 520 is set to connect tube 515 to inner needle 260 via tube 290 and sample loop 530. Syringe 500, which may be of the type commercially available from a source such as Hamilton, is activated by stepper motor 505 connected to plunger 502 and controlled by the onboard microprocessor. Barrel 501 is fixed in position. In the preferred embodiment several different syringe capacities may be interchanged to effect changes in capacity, precision, accuracy. A zero position sensor (not shown) is used as a reference from which the syringe is stepped outward or inward with the program algorithm equating the desired displacement for the operation. The capacity of the syringe being used is inputted by the operator of the autosampler and stored in memory.

As the syringe plunger 502 is withdrawn, fluid is aspirated from the sample vial into tube 290 and, thereafter into the sample loop 530. The sample loop can be either fully or partially filled with the sample liquid depending on the amount of sample available and the needs of the analysis. Partial loop filling may be utilized when the sample volume is very small. After the desired amount of liquid is drawn into the sample loop, movement of syringe plunger 502 is stopped.

The liquid which has thus been withdrawn from the sample vial 77 can either be injected into the chromatography column 700, or can be introduced into another vial as part of a sample preparation routine. If it is desired to introduce the liquid withdrawn from the sample vial into another vial as part of a sample preparation routine, the other vial is first positioned under the needle/lifter assembly as described below and lifted into position. The syringe plunger 502 is then moved forcing the liquid into the vial.

To inject the sample into column 700, sample loop injection valve 520 is rotated into a position connecting high pressure pump 550 to one end of sample loop 530 and the other end of sample loop 530 to the input of column 700. As is well known, the sample is separated into components as it traverses the column. These components are then directed to a detector 710 which may be of a variety of known types.

Four-way valve 510 may be rotated to connect a solvent reservoir 560 with syringe 500 via tube 565. When this connection is made, solvent from the reservoir 560 may be drawn into the syringe 500. If four-way valve 510 is then rotated to connect syringe 500 with tube 515, the solvent may then be used to wash needle 260.

Four-way valve 510 may also be rotated to connect line 575 with either line 515 or 565. Connection with line 575 enables the operator to manually prime/purge the hydraulic lines as needed. The need for such purging/priming occurs in all systems from time-to-time to remove gas/vapor bubbles or to change the solvent being used. The ability to accomplish this quickly and efficiently is a significant improvement over the prior art.

FIGS. 3-6 are detailed drawings of the vial lifter/needle assembly 80. Vial lifter 200 is hollow and is connected at its bottom end to a waste solvent drain line 210, which may be of any common flexible tubing compatible with the solvents being used in the system. Arm 220 connects vial lifter 200 with lead screw 230 and guide rods 231. Lead screw 230 is powered by motor 240 to raise and lower the vial lifter 200 by the action of floating nut 232 (shown in FIG. 5).

The needle assembly comprises concentric inner and outer hollow needles 260 and 270 respectively. A sealed fluid path to inner needle 260 runs through needle housing 280 and out through tube 290. Tube 290 is connected by a series of valves and tubes to a syringe, a sample loop, a solvent supply and to the liquid chromatography column, as described in detail above in reference to FIG. 2. A source of pressurized gas (not shown) is connected to the outer needle 270, which may also be vented to atmosphere. Arm 300 holds needle assembly 280 in a stationary position with respect to guide rods 231, lead screw 230 and floor 310.

Vial stabilizer 320 has a central aperture allowing it to move freely with respect to both the inner and outer needles and is designed to receive and engage the top of a vial as it is lifted by the vial lifter 200. Vial stabilizer 320 is attached to arm 325 which moves up and down on guide rods 231.

FIG. 4 shows the vial lifter/needle assembly in the raised position with a vial lifted onto the needle. Rack 50 is rotated and translated to bring the chosen vial into the proper position beneath the vial lifter as specified by the operator's intructions. Each vial recess 70 in rack 50 has an aperture at its bottom wide enough to allow the passage of vial lifter 200. Motor 240 is activated turning lead screw 230 and causing vial lifter 200 to move in an upward direction by the action of floating nut 232. Vial lifter 200 contacts the bottom of vial 77 and lifts it. The top of vial 77 contacts vial stabilizer 320 before the vial leaves rack 50 and holds it in a stable position. Vial stabilizer 320 then moves upwardly under the force of the vial lifter 200 as transmitted through the vial 77. During this upward motion, vial stabilizer 320 exerts a constant force on the vial 77. After the vial top engages the vial stabilizer 320, inner needle 260 and outer needle 270 sequentially penetrate vial septum 78 as a result of the continued upward motion of the vial lifter. At or near the point of maximum upward motion of the vial lifter 200, inner needle 260 contacts the bottom of vial 70 thereby ensuring that all the liquid in the vial is available for use. As described in detail below, inner needle 260 is spring-loaded so that it will travel upwardly a small distance in the event it contacts the bottom of the vial before the vial lifter has reached its maximum upward extension.

Note that the outer needle comes to rest in the vial head space above the level of the liquid. While the vial is being lifted a burst of pressurized gas can be directed through the outer needle to blow clean the space between the two needles, to blow any liquid off the inner needle, and to blow clean the surface of the septum 78. Pressurized gas can also be directed into the head space as part of a leak test routine or to saturate the sample with a desired gas as part of a sample preparation routine. Finally, outer needle 270 can be vented to atmosphere during sample aspiration to prevent the formation of a vacuum as sample is removed.

Figure 3:
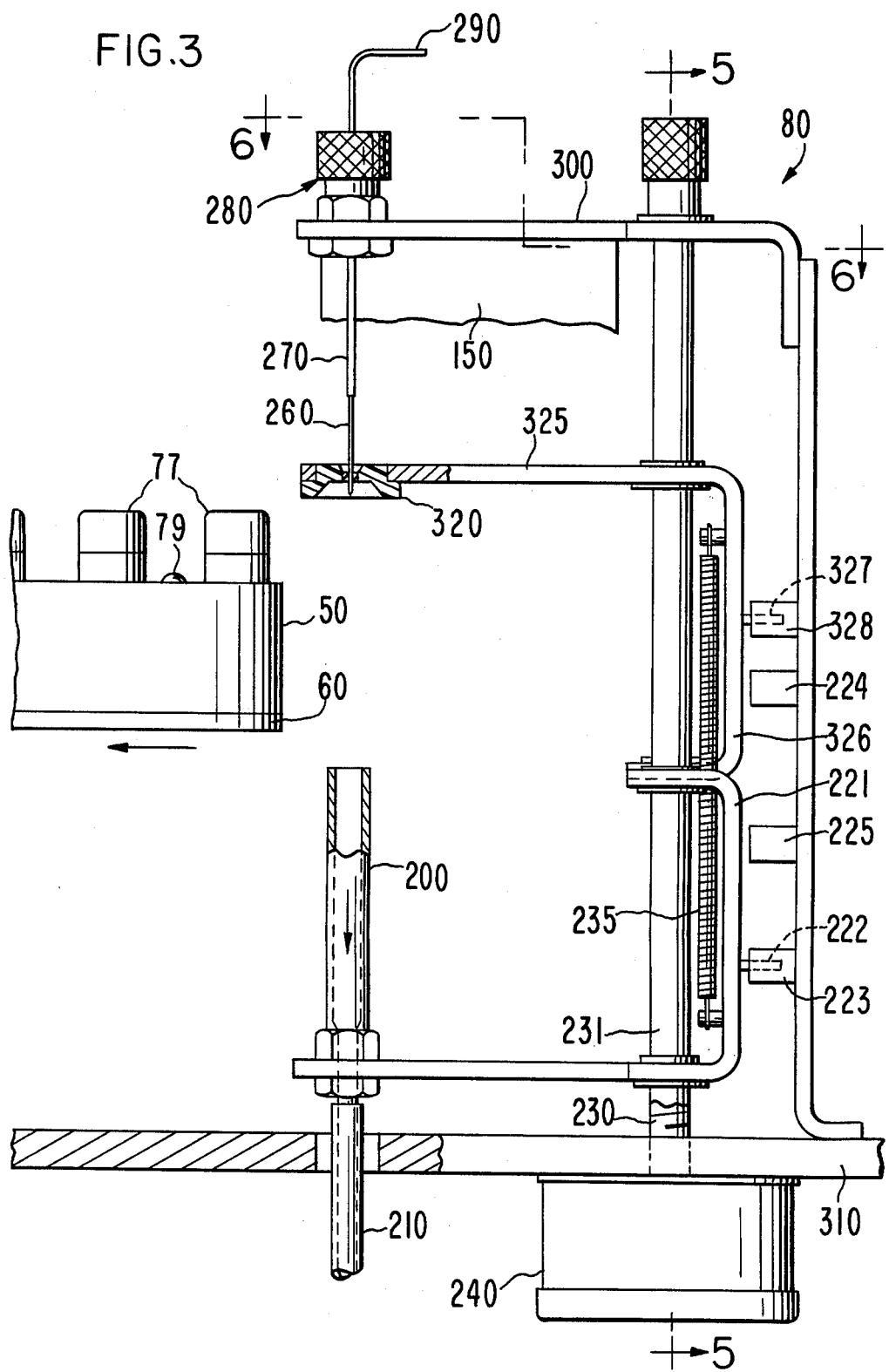
FIG. 3 is a cross-sectional side view of the vial lifting/needle assembly mechanism of the present invention in the rest position.

Rack 50 can be translated out of the way of vial lifter/needle assembly 80 as shown in FIG. 3. With the rack out of the way, vial lifter 200 can be raised upwardly to a point where the inner hollow portion of the lifter surrounds the end of the inner needle 20. In this position vial lifter 200 is able to receive waste solvent used to wash the needle between sample withdrawals. While the waste solvent is being discharged into the hollow vial lifter, carousel 60 can be rotated to the next position ready to be translated to a position under the needle assembly 80 as soon as the wash operation is complete. Multiple wash cycles can be programmed by the operator as desired, if, for example, the desired volume of wash exceeds the capacity of the syringe.

Figure 5:
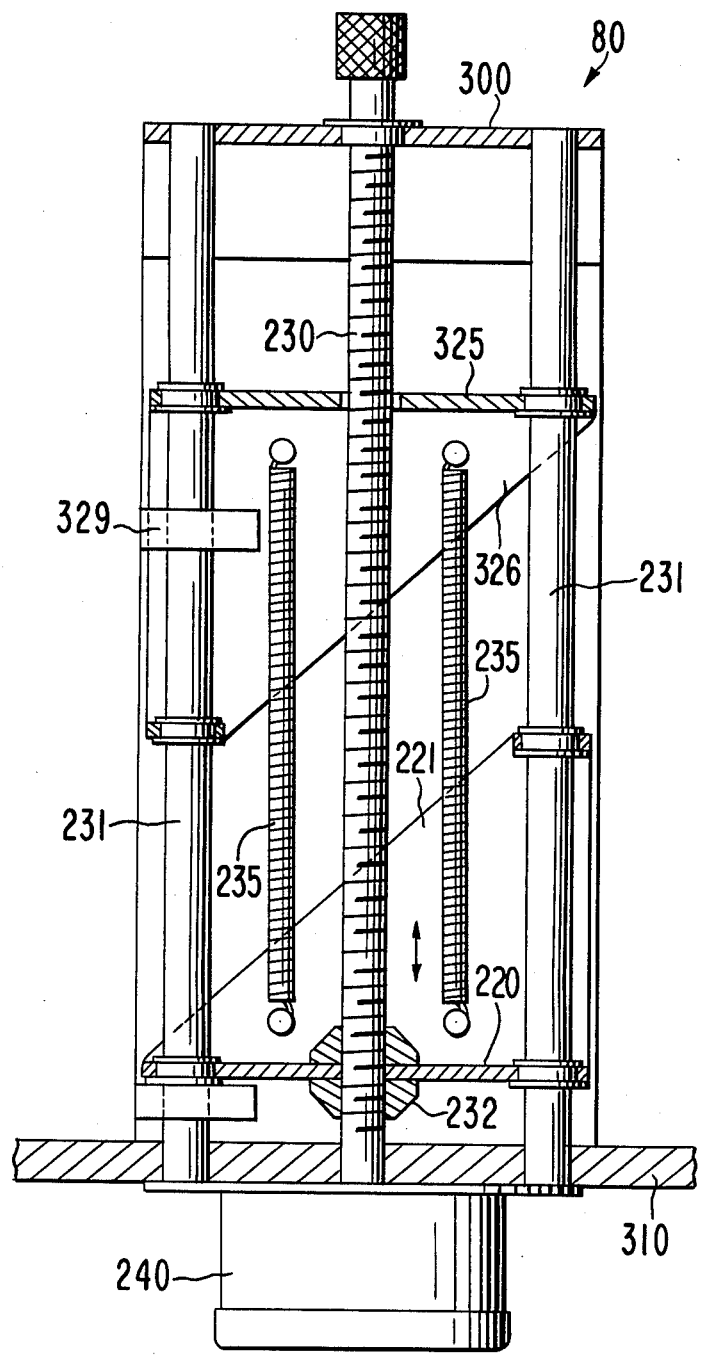
FIG. 5 is a cross-sectional rear view of the vial lifting assembly along line 5—5 of FIG. 3.

Arms 220 and 325 are attached to triangular vertical sections 221 and 326 respectively as shown in FIG. 5. Each of these sections has a flag which is used to interrupt the light path of optical switch assemblies. The lowest optical sensor 223 is interrupted by the lower flag 222 mounted on section 221 when the vial pusher 200 is in the fully down position. This alerts the control unit that the carousel may be moved.

Stop 329 limits the downward motion of section 326, and thereby, vial stabilizer 320. Stop 329 is set at a position such that the vial stabilizer 320 clears the top of the vials in the racks on the carousel, but is low enough to engage the vial being elevated before it leaves recess 70. An upper optical sensor 328 detects the presence of flag 327 mounted on section 326 when the vial stabilizer is in the down position. This alerts the unit that the vial has completely cleared the needle and the carousel may be moved. Upper section 326 is connected to lower section 221 by one or more springs 235 to cause a constant downward tension between the two when a vial is being elevated. It should be noted that, in the preferred embodiment, the vial stabilizer is not independently driven upward, but rather is forced upward by contact with a vial being lifted, or if no vial is present, by contact between section 221 and 326.

When the vial is fully elevated lower flag 222 interrupts the light path of optical sensor 224 alerting the processor to stop the lifting action of motor 240. As the vial is lowered the tension in spring(s) 235 cause the upper section 326 and vial stabilizer 320 to follow. When the upper section 326 reaches stop 329 the vial septum 78 is free of the inner needle 260 and the vial 77 descends into the rack by its own weight as the vial lifter 200 retracts to its rest position.

When no vial is present in the vial lifter path, the lower section 221 can ascend vertically to a point where flag 222 interrupts optical sensor 328. It is then stopped so the vial lifter 200 can receive waste wash solvent discharged from inner needle 260. Section 221 attached to vial lifter 200 encounters section 326 attached to vial stabilizer 320 during this upward motion and pushes it upward as it proceeds. The system first sends lower section 221 to the point where flag 222 interrupts optical sensor 224. When it arrives at this point, flag 327 on upper section 326 has been moved above optical sensor 328. This condition alerts the processor to then direct lower section 221 to proceed upward until flag 222 encounters optical sensor 328.

If in the process of sampling vials the unit attempted to remove a sample from an unoccupied vial position, air might be drawn into the system and injected into the column. Likewise, it is equally undesirable to discharge liquid to an unoccupied rack recess. To prevent this the unit takes an inventory as described below and will not go to an unoccupied position. As a backup measure the vial lifter/needle assembly 80 has a means for independently determining the presence of a "no-vial" condition. An optical sensor 225 is located above sensor 223. When the vial lifter raises a vial the vial encounters vial stabilizer 320 and moves flag 327 away from optical sensor 328 before flag 222 on lower section 221 reaches optical sensor 225. If, however, no vial is present, flag 222 reaches optical sensor 225 while flag 327 remains at optical sensor 328. The simultaneous interruption of both optical sensors alerts the unit that a "no-vial" condition exists and vial lifter 200 is instructed to descend. This feature is disabled during the wash cycle described above.

FIG. 8 is a cut away view of needle housing 280 containing the mechanism for spring-loading the inner needle 260 and providing a portion of the fluid path to outer needle. The inner needle 260 extends above the outer needle 270 and the needle housing 280 where it passes optionally through a seal 410. The seal 410 is required when the outer needle is used to transmit pressurized gas as described above so that the gas does not leak to atmosphere. Tube 440 connects outer needle with the source of pressurized gas and/or to the atmosphere.

The upper end of inner needle 260 is connected to tube 290. The inner needle is provided with a flange 420 which can abut upper and lower stops defining the range of travel. This range of travel should exceed the acceptable variation in vial bottom thicknesses. A spring 430 provides a light downward force which keeps the inner needle at the lower stop when not otherwise loaded.

As the vial is impaled coaxially on the inner needle 260, it may be displaced partially or fully to the upper stop, depending on the spring constant of spring 430 and the force necessary to penetrate the septum 78. After the outer needle 270 penetrates the septum, all force against the inner needle 260 is released and it returns to the lower stop. Thereafter, as the vial continues its upward motion the inner needle contacts the inner surface of the vial bottom and is displaced upward to accommodate the final vial position.

The mechanism which establishes the position of the lower end of the inner needle 260 relative to the fully extended vial lifter 200 is adjusted so that the inner needle 260 will just make contact with the bottom of a vial 77 with the smallest bottom thickness expected. The range of displacement will then accommodate any greater vial bottom thickness for which the design was intended. The free end of the inner needle 260 and tube 290 are of sufficient length and geometry to be flexible to allow the required tip motion without requiring any motion of the sample loop/injection valve. Tube 290 may be an integral extension of the inner needle. As is well known is liquid chromatography, every effort should be made to minimize the dead volume of the hydraulic system.

FIG. 8 shows only one approach to the spring-loaded inner needle design; other methods of construction could provide the same features. For example, the needle flange and spring could easily be located outside of the needle housing 280. In such a design it would be easy to provide the upper portion of the inner needle 260 with a microswitch, flag or similar feature which, upon slight upward displacement, would signal the vial lifter to stop its upward motion. Such a system could be programmed to ignore any signal caused by the upward motion of the needle caused by penetration of the septum. This approach would minimize the amount of displacement needed for the inner needle.

Every time the cover of the apparatus is opened, the autosampler inventories all racks and vial positions before proceeding to any sample manipulation. The vial sensing mechanism is detailed in FIG. 7. The carousel is aligned with optical sensing unit comprising an upper portion 150 having a series of light-emitting diodes (LEDs) 120 mounted therein and a lower portion 100 having a corresponding series of photodetectors 110 in vertical alignment with the LEDs 110. If a vial is present in a vial recess, the light path is interrupted informing the autosampler. This information is then stored in memory. In addition, the racks have holes 74 which align with another LED/photodetector pair. By placing plugs 79 in the holes of the racks, the racks can be coded. Holes in the carousel plate 60 correspond to the rack and vial recess holes completing the optical path. In addition, a separate optical sensing mechanism (not shown) is used in conjunction with an encoded disk (not shown) attached to carousel plate 60. This combination is used to identify the absolute angular position of the carousel plate 60.

The inventory or map of racks and vials is then stored in memory where, in accordance with the program stored in ROM, it is used to implement the operator's sampling instructions and to prevent any inadvertent attempt to withdraw fluid from or discharge fluid to a vial position not containing a vial. In addition, by numbering the racks, inadvertent rack substitution during execution of a sampling routine is avoided.

FIG. 9 is a fragmentary plan view of the carousel plate 60 and vial racks 50 showing the details of the structure for securely holding the racks in position. In the preferred embodiment of the present invention up to seven racks, each with three rows having five vial receiving recesses 70 may be secured to the carousel 60 for a total of 105 vial positions. In addition, one priority vial position is available. The unit may be operated with any desired number of racks up to the maximum of seven. The racks may be coded by inserting plugs in holes 74 which are optically read as described above. In the preferred embodiment there are five such holes providing 32 possible combination of plug codes.

Racks 50 are held in a secure position on carousel 60 by the combined action of clips 55 engaging pins 65 and posts 67 engaging rack side recesses 57. Each rack 50 is held at either side by post 67 in a side recess 57, preventing any side-to-side motion of the rack. As shown best in FIG. 10, post 67 comprises a lower cylindrical portion 68 and an upper button-shaped portion 69. Side recesses 57 have a lower lip 58 which extends below button 69 when the rack 50 is in position on the carousel 60. This prevents the rack from any upward motion after being placed in position. Finally, posts 67 are designed to engage side recesses 57 at a position just shy of the point that clip 55 has fully engaged pin 65. This causes clip 55 to maintain an inward-directed force and further helps to prevent any "play" in the mounted racks.

I claim:

1. An autosampler for use in liquid chromatography comprising:
   carousel means for holding at least one vial rack having a plurality of recesses for receiving liquid-containing vials;
   a fixed needle assembly for withrawing liquid from said vial;
   vial lifter means in vertical alignment with said fixed needle assembly for lifting individual vials out of said vial recesses and impaling said vials on said needle assembly;
   means for moving said carousel to align said vial recesses with said vial lifter means;
   said needle assembly comprising a sample needle having a limited range of vertical travel such that the needle will move upward when it contacts the bottom of a vial being lifted.

2. The autosampler of claim 1 further comprising spring means for maintaining said sample needle at the downward extreme of said range of vertical travel in the absence of upward force on said sample needle.

3. The autosampler of claim 2 wherein said range of travel covers the range of variations in bottom thicknesses of the vial types and vial manufacturing tolerances of the vials intended for use is said autosampler.

4. The autosampler of claim 3 wherein said vial lifting means is elevated to a set point whenever it lifts a vial onto said needle assembly.

5. The autosampler of claim 4 wherein said set point of maximum upward travel of said vial lifter is adjusted so that said sample needle touches the bottom of a vial of minimium expected bottom thickness without upward displacement.

6. The autosampler of claim 2 further comprising a fixed outer needle concentric with said sample needle, said outer needle extending into vial head space when said sample needle engages said vial bottom.

7. The autosampler of claim 6 wherein said outer needle is connected to a source of pressurized gas.

8. The autosampler of claim 7 further comprising means to direct a burst of said pressurized gas through said outer needle in the space between said outer needle and said inner needle as said vial is being lifted onto said needle assembly.

9. An autosampler for use in liquid chromatography comprising:
   carousel means for holding at least one vial rack having a plurality of recesses for receiving liquid-containing vials;
   a fixed needle assembly for withdrawing liquid from said vials;
   vial lifter means in vertical alignment with said fixed needle assembly for lifting from below individual vials out of said vial recesses through apertures in the bottoms of said vial recesses and impaling said vials on said needle assembly;
   means for rotating and translating said carousel to align said vial recesses with said vial lifter means;
   said vial lifter means being adapted to receive waste wash solvent discharged from said needle;
   means for disposing of said waste wash solvent received by said vial lifter.

10. The autosampler of claim 9 wherein said vial lifter is generally cyclindrical and hollow.

11. The autosampler of claim 10 wherein said means for disposing of said waste wash solvent comprises a drain line connected the bottom of said vial lifter.

12. In an autosampler for use in liquid chromatography comprising:
   carousel means for holding at least one vial rack having a plurality of recesses for receiving liquid-containing vials;
   a fixed needle assembly comprising a needle for withrawing liquid from said vial;

vial lifter means in vertical alignment with said fixed needle assembly for lifting from below individual vials out of said vial recesses through apertures in the bottoms of said vial recesses and impaling said vials on said needle assembly;

means for moving said carousel to align said vial recesses with said vial lifter means;

vial stabilizer means having a central aperture allowing the passage of said needle, which engages the top of a vial being lifted from said vial recess before said vial leaves said recess and which moves upward with said vial as it is lifted out of said vial recess and impaled on said needle assembly applying a substantially constant downward force on said vial top while they are engaged.

13. An autosampler for use in liquid chromatography comprising:

carousel means for holding a plurality of vial racks having a plurality of recesses for receiving liquid-containing vials, said liquid containing vials being adapted to be covered by septa;

a fixed needle assembly comprising concentric inner and outer needles, said inner needle for withrawing liquid from and discharging liquid to said vial and said outer needle for venting head space of said vials to the atmosphere and for flowing pressurized gas;

vial lifter means in vertical alignment with said fixed needle assembly for lifting from below individual vials out of said vial recesses through apertures in the bottoms of said vial recesses and impaling said vials on said needle assembly, said vial lifter being adapted to receive liquid waste discharged from said inner needle;

means for moving said carousel to align said vial recesses with said vial lifter means, and to move said carousel away from alignment with said vial lifter;

vial stabilizer means having a central aperture allowing the passage of said needle, which engages the top of a vial being lifted from said vial recess before said vial leaves said recess and which moves upward with said vial as it is lifted out of said vial recess and impaled on said needle assembly applying a substantially constant downward force on said vial top while they are engaged;

said inner needle having a spring-loaded limited range of vertical travel such that said inner needle will move upward when it engages the bottom of a vial being lifted.

14. The autosampler of claim 13 further comprising a sample loop, an injection valve and a syringe connected to said inner needle so that liquid in said vial can be drawn into said sample loop by said syringe and thereafter injected into a high pressure liquid chromatography column.

15. The autosampler of claim 14 further comprising a solvent resevoir and a four-way valve connected to said syringe whereby said syringe can withdraw solvent from said resevoir, and thereafter use said withdrawn solvent to wash said inner needle, and whereby said four-way valve can be set to allow manual priming and purging of the system.

16. The autosampler of claim 13 further comprising a microprocessor control unit and resident control programs allowing random access to sample vials and complex sample manipulations.

17. The autosampler of claim 16 further comprising means to code and identify the sample racks placed on the carousel and to inventory which vial recesses are occupied by vials.

18. The autosampler of claim 17 further comprising means to store information about the identity of racks and about the inventory of vials in memory and means to use said stored information to prevent the autosampler from attempting to withdraw fluid from or discharge fluid to an unoccupied vial recess.

19. An autosampler for use in liquid chromatography comprising:

carousel means for holding at least one vial rack having a plurality of recesses for receiving liquid-containing vials; a fixed needle assembly for withdrawing liquid from said vials;

vial lifter means in vertical alignment with said fixed needle assembly for lifting from below individual vials out of said vial recesses through apertures in the bottom of said vial recesses and impaling said vials on said needle assembly;

means for moving said carousel to align said vial recesses with said vial lifter means;

vial stabilizer means for engaging the tops of said individual vials as they are lifted out of said vial recesses, said vial stabilizer means being adapted to travel upward with said individual vials after engaging the tops of said vials; and, means for detecting the absence of a vial in a vial recess comprising means for detecting that said vial stabilizer has not engaged the top of a vial when said vial lifter is being elevated.

* * * * *